Figure 1:
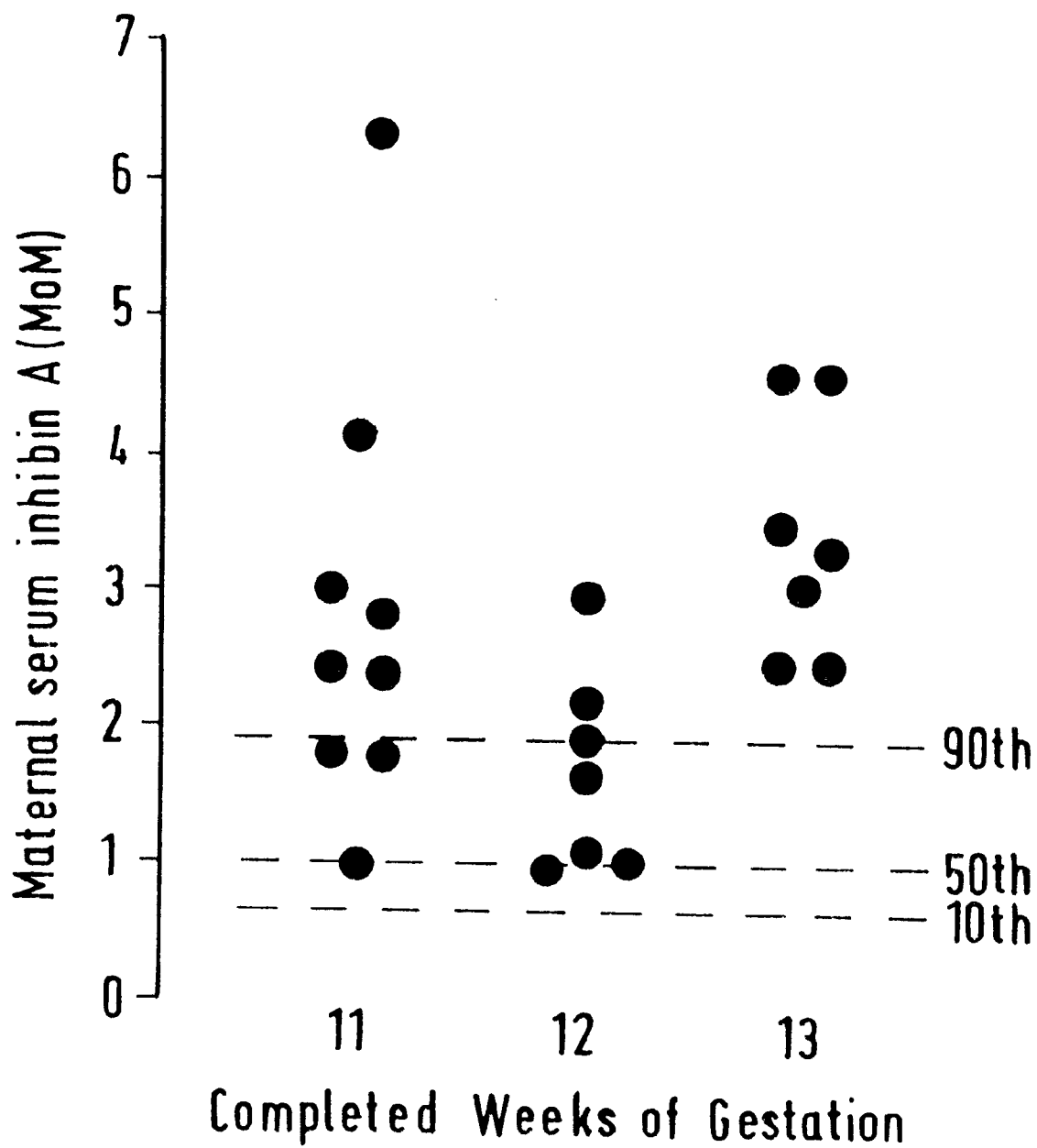

United States Patent [19]
Groome et al.

[11] Patent Number: 5,952,182
[45] Date of Patent: *Sep. 14, 1999

[54] METHOD OF GENETIC TESTING

[75] Inventors: Nigel Patrick Groome, Oxfordshire, United Kingdom; Euan Morrison Wallace, Victoria, Australia

[73] Assignee: Oxford Brookes University, Oxford, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/737,986

[22] PCT Filed: May 22, 1995

[86] PCT No.: PCT/GB95/01164

§ 371 Date: Feb. 11, 1997

§ 102(e) Date: Feb. 11, 1997

[87] PCT Pub. No.: WO95/32431

PCT Pub. Date: Nov. 30, 1995

[30] Foreign Application Priority Data

May 24, 1994 [GB] United Kingdom ............... 9410345

[51] Int. Cl.⁶ .................. G01N 33/53; G01N 33/543; C07K 16/00
[52] U.S. Cl. .................... 435/7.1; 435/7.94; 436/63; 436/65; 436/86; 436/87; 436/501; 436/518; 530/388.24; 424/139.1; 424/141.1
[58] Field of Search .................. 530/388.24; 424/139.1, 424/141.1; 435/7.1, 7.94; 436/63, 65, 86, 87, 501, 518, 811, 817

[56] References Cited

PUBLICATIONS

Groome et al., Hybridoma., vol. 10., Issue. 2., pp. 309–316., 1991.
Groome et al., Journal of Immunological Methods., vol. 165., pp. 167–176., 1993.
J. M. M. Van Lith et al., Prenatal Diagnostics., vol. 12., pp. 801–806., 1992.

*Primary Examiner*—Ponnathapura Achutamurthy
*Assistant Examiner*—P. Ponnaluri
*Attorney, Agent, or Firm*—Clifford W. Browning; Woodard, Emhardt, Naughton, Moriarty & McNett

[57] ABSTRACT

Elevated levels of Inhibin-A in maternal serum or plasma have been shown to indicate the presence of Down's Syndrome. The assay method comprises the use of a monoclonal antibody specific for at least part of the inhibin-A β sub-unit (βA), and another monoclonal antibody specific for at least part of the Inhibin-A α sub-unit. The βA antibody is used to capture Inhibin-A from the test sample, and the α sub-unit antibody is used as the detection antibody and is linked to a detectable marker. The method is carried out in the first or second trimester as a screening test to select patients for subsequent diagnostic testing.

21 Claims, 2 Drawing Sheets

METHOD OF GENETIC TESTING

This invention relates to the detection of possible genetic abnormalities and more particularly to those of Down's Syndrome.

Prenatal screening for Down's syndrome has become an important and established part of modern antenatal care. At present, most screening programmes depend upon maternal age in combination with the measurement of human chorionic gonadotrophin (hCG) and α feto-protein (AFP), with or without unconjugated oestriol (uE3), in maternal serum at 16 weeks gestation. Such an approach will detect approximately 65% of Down's affected pregnancies for an amniocentesis rate of 5%. However, it has long been hoped that improvements in screening might increase this detection rate, while minimising the amniocentesis rate, and also allow testing to be performed earlier in pregnancy. To this end, it was recently reported that inhibin, a heterodimeric glycoprotein produced by various tissues, including the placenta, was elevated in the second trimester in maternal serum from Down's syndrome pregnancies compared to normal pregnancies (van Lith et al. 1992. Second-trimester maternal serum immunoreactive inhibin as a marker for fetal Down's syndrome, Prenatal Diagnosis 12, 801–806; and Spencer, K. et al. 1993. Elevated levels of maternal serum inhibin immunoreactivity in second trimester pregnancies affected by Down's syndrome, Annals of Clinical Biochemistry 30, 219–220).

In addition, a number of fetal and placental proteins have undergone initial evaluation of their usefulness as first, rather than second, trimester maternal serum markers for Down's syndrome (Macintosh M. C. M. and Chard, T., 1993, Biochemical screening for Down's syndrome in the first trimester of pregnancy, Fetal and Maternal Medicine Reviews 5, 181–190 and references therein).

Screening earlier in pregnancy, in the first trimester, would have considerable advantages over the current second trimester timing. Several maternal serum markers, including α fetoprotein (AFP), b-subunit of human chorionic gonadotrophial (β-hCG). Pregnancy-associated placental protein A (PAPP-A) have been assessed as first trimester markers of which β-hCG appears the most promising of these to date. A combination of maternal age, β-hCG and AFP has been predicted to otter a detection rate of 54% for an amniocentesis rate (or false positive rate—FPR) of 5% (Aitken et al, 1993, Biochemical screening for chromosome abnormalities and neutral tube defects in the first trimester, Journal of Medical Genetics 30,336). Clearly, there is still a need for a more reliable test with improved sensitivity and specificity which would preferably be applicable to both the first or second trimester, but especially the former.

It has now been established that enhanced levels of a particular species of the hormone Inhibin in maternal body fluids are indicative of the possible presence of fetal abnormality of this kind.

The hormone Inhibin is known to be involved in human and animal reproduction although its precise role is not yet established. It is now known that there is a "family" of inhibins known as Inhibin A and Inhibin B. These molecules are dimers composed of two sub-unit monomers. Inhibin-A consists of two protein sub-units, termed α and βA, which are joined together by disulphide bonds.

European patent 185,034, dating from applications in 1984 and 1985, precedes the discovery of a family of inhibins and discloses one dimeric form of inhibin, which it identifies in terms of molecular weight, sub-unit structure, and other properties. EP 185,034 sizes one sub-unit at molecular weight 14,000+/−2000 kilodaltons (12K or 14K) and the larger sub-unit as a 44K molecule. Later research suggests that the primary active form of dimeric inhibin-A in biological fluids is of size 32K, corresponding to a 12K βA and a 20K α sub-unit. The 32K inhibin is the mature form produced by post-translational processing of precursor forms of molecular weight 65K and 56K. Immunoreactive α monomer also circulates in the body, a factor which complicates the assay of inhibin. It is common to refer to "inhibin forms" as signifying the totality of circulating inhibin proteins.

The complex nature of Inhibin and the fact that both monomeric and dimeric forms circulate in the body presents formidable problems of analytical determination and biological interpretation of research results. For example, previously reported immunological methods of measurement of Inhibin have not enabled clear conclusions to be made because immunoreactivity measurement does not discriminate between the various molecular species described above, and is therefore not a reliable guide to functional bioactivity. The Van Lith et al and Spencer et al publications mentioned above are the only two publications describing the use of immunoreactive Inhibin in the detection of Down's syndrome in the second trimester. Both of these studies utilised a commercial enzymometric assay (Medgenix, High Wycombe) with two anti α subunit antibodies. Both studies reported poor discrimination due to a wide distribution of results in both control and Down's syndrome samples.

The present invention comprises a method of testing for indications of Down's syndrome which comprises measuring the level of Inhibin-A in maternal body fluid preferably by means of an assay which is specific for Inhibin-A.

In accordance with the invention, levels of all molecular forms of dimeric inhibin-A are preferably measured, irrespective of molecular size. However, we do not preclude the possibility that it may be sufficient for the purposes of the present invention to assay specifically for the mature 32K form of the dimeric protein.

Any convenient and accurate method of assay of dimeric inhibin-A may be used for the diagnostic purposes of this invention. Various assays are known but some, in their present form described in the literature, are less suitable than the preferred assay which will be described in detail hereinafter. For example Baly et al recently reported development of two-site assays for various inhibin forms using monoclonal and polyclonal antibodies raised to recombinant inhibin. (Baly, D. L., Aldisim, D. F., Krummer, A., Woodruff, T. K., Soules, M. R., Chen, S. A., Fendly, B. M., Bald, L. N., Mathet, J. P. & Lucas, C. (1993) Development of a specific and sensitive two-site enzyme-linked immunoadsorbent assay for measurement of inhibin-A in serum. Endocrinology, 132, 2099–2103). However, the detection limit of their assay for dimeric inhibin-A was 1000 pg/ml of serum, and in the data presented, inhibin could not be detected in all the samples, even from women undergoing gonadotrophin therapy.

The preferred assay is one based on monoclonal antibody technology. Thus the assay method may comprise the use of antibodies specific for at least part of the Inhibin-A α and βA sub-units.

The βA antibody is preferably derived from a hybridoma prepared using as immunogen a synthetic peptide corresponding to a part of the βA sub-unit. The α sub=unit antibody is preferably derived from a hybridoma prepared using as immunogen a synthetic peptide corresponding to a part of the α sub-unit. Advantageously, the βA antibody is used to capture Inhibin from the test sample and the α sub-unit antibody is used as the detection antibody and is linked to a detectable marker e.g. an enzyme. Fragments of these antibodies having the same specificity as the whole antibodies may also be used. The term 'antibody' is used herein to include such fragments.

The antibodies used in the assay are derived from hybridomas produced by methods which have been described in the literature (Groome et al 1990 Monoclonal and polyclonal antibodies reactive with the 1–32 amino terminal peptide of 32K human inhibin. Hybridoma, 9, 31–41; and Groome, et al, 1991, Preparation of monoclonal antibodies reacting with the beta-A subunit of human ovarian inhibin. Hybridoma, 10, 309–316). The assay has also been described by Groome, et al, 1993, Immunoassays for inhibin and its subunits. Further applications of the synthetic peptide approach, J. Immunol. Methods 165, 167). These Groome et al publications are incorporated herein by reference.

The preferred assay procedure, to avoid interference from heterophile antibodies, is to use the Fab fragment of the monoclonal antibody to the inhibin α sub-unit attached to an enzyme rather than the whole antibody molecule. The inclusion of 5% (v/v) mouse serum and 5% w/v) Triton×100 in the assay diluent are also important in maintaining the specificity of the assay.

The antibodies and a detailed protocol are available from Serotec Ltd. 22 Hankside, Station Approach, Kidlington, Oxford, OX5 1JE.

The immobilization of the capture antibody (that to the β A sub-unit) on hydrazide plates (Avidplate-HZ from Bioprobe) rather than by passive adsorption on ordinary microplates is important in retaining a high density of functional antibody essential to give good recoveries of inhibin from serum and plasma. In an earlier version of the assay it appeared that other methods of immobilizing the anti-β A antibody gave similar results for standards diluted in assay buffer. When these were compared with the hydrazide plates procedure the latter gave much better recoveries of recombinant inhibin spiked into human sera.

SPECIFICITY OF THE ASSAY

Until recently it was not clear whether the assay as described would be able to distinguish inhibin-A from inhibin B. The synthetic peptide sequence from the human β A sub-unit used as an immunogen to make the E4 antibody has homology with the corresponding sequence from the beta B sub-unit and the two peptides both react well with the antibody. Recently with samples of recombinant materials we have established that inhibin-B, activin A and activin B all have very low cross-reactivity in our assay as shown below.

| Percentage cross reaction | |
|---|---|
| Inhibin-A | 100 |
| Inhibin-B | 0.012 |
| Activin A | <0.002 |
| Activin B | >0.001 |

Thus this assay in practice can be regarded as measuring specifically forms of inhibin-A in human serum and plasma samples. The assay does not detect free forms of the α-sub-unit.

The method of this invention may be used with appropriate maternal body fluids e.g. serum or plasma. The method is effective when carried out in the first or second trimester. The method may be viewed as a screening test to select patients for subsequent diagnostic testing. In Down's syndrome pregnancies, the median level of inhibin-A was noted to be more than twice that in normal pregnancies. Importantly, the degree of difference was maintained across both first and second trimesters. This is the first report of the use of a dimeric inhibin-A assay in pregnancy and the subsequent successful application of the assay to the detection of Down's syndrome in the first and second trimester of pregnancy. It will be shown that using the measurement of inhibin-A alone in the first trimester, detection rates that compare very favourably with currently available combinations are possible. Also, in the second trimester when used alone inhibin-A offers high rates of detection and when combined with current screening will significantly improve detection rates. Prior to describing these data in detail, the methodology pertaining to the production of monoclonal antibodies and to the assay will be described.

As indicated previously, the production of hybridoma cell lines which secrete the antibodies has been described in the literature. Further directions for preparing the most effective cell-lines are described in the following section.

Factors important to success in making a high affinity antibody useful for immunoassay The capture antibody is required to have a very high affinity for inhibin, as evidenced by its performance in the two-site assay for dimeric inhibin described later. The affinity of the antibody is further increased when the inhibin in standards and samples is preoxidised with hydrogen peroxide. This oxidises two methionine residues in the region of the epitope. (Knight, P. G. and Muttukrishna, S. (1993) Measurement of dimeric inhibin using a modified two-site IRMA specific for oxidised (met 0) inhibin Poster at Serono symposium on Inhibin and Inhibin-related substances, Siena June 1993).

Most anti-peptide antibodies raised to internal peptide sequences react with the parent protein with low affinity. The important factors are:

1. The frequency of clones making such good antibodies is low.

2. It is recommended to generate as many peptide-reactive clones as possible and to screen rigorously on the native molecule to select clones which react with the whole molecule.

3. Four intravenous doses of tuberculin/peptide conjugate should be given on each of the four days before spleen cell removal. We have routinely used up to 200 micrograms of peptide per injection and have supplemented this with intraperitoneal injections on occasions when the success of the intravenous injection was in doubt. The spleen of immunized mice is invariably large indicating hyperimmunization.

4. We have noted a particular value to tuberculin as a carrier for synthetic peptide immunizations in mice primed three weeks earlier with 1 dose of human BCG vaccine (Glaxo) given subcutaneously. The advantage is that BCG vaccination gives a high frequency of helper T cells recognizing tuberculin without generating a lot of irrelevant B cells which go on to give unwanted hybridomas. With conventional carriers after an aggressive immunization scheme such as that described most of the clones growing after the fusion would be to the carrier making it much harder to identify the clones making antibody to the peptide immunogen.

The following materials and methods have been used.
Preparation of Antibody to βA sub-unit (E4)
Coupling of Peptides to carrier protein The location on the human inhibin β A inhibin subunit of the seven peptides used for immunization are shown in FIG. 1 of Groome et al Hybridoma 10 309–316 (1991). The peptides were made using Fmoc chemistry and contained a single cysteine residue which was either part of the natural sequence or added only to facilitate coupling. Coupling of each peptide to tuberculin via the —SH group was made using heterobifunctional ester using protocols obtained in a kit available from Cambridge Research Biochemicals, Button End Industrial Estate, Harston, cambridge, U.K. or by other well-known methods.

Immunization and Screening of mice

Male Balb/c mice were initially primed with one dose of human BCG vaccine (Glaxo). Mice then received four monthly subcutaneous boosts of 50 micrograms of each peptide as a tuberculin conjugate in Freund's incomplete adjuvant. Six mice were immunised with each peptide as a tuberculin conjugate. When tested by ELISA on plates coated with bovine 32 KDa, inhibin peptides 1, 3, 4 and 5 gave no responses distinguishable from unimmunized mice. Peptide 6 produced one medium responder (A=0.4), peptide 2 produced two medium responders (A=0.4 and A=0.8) and peptide 9 produced two high responders (Absorbance greater than 2) and four medium responders (A=0.9, 1.0, 1.4, 0.7). The highest responding mouse was assessed by ELISA and each of the last four days before fusion it received 50 micrograms of peptide as a tuberculin conjugate intravenously in saline.

ELISA screening protocols (test for antibodies)

Purified 32 KDa bovine inhibin was purchased from Peninsula laboratories and covalently attached to Cobind (Polyfiltronics) plates according to the manufacturers instructions. A coating concentration of 0.1 micrograms per ml was used in phosphate buffered saline (PBS) for 5 hrs at 37° C. These plates are no longer available but similar results have been obtained with maleic anhydride activated plates (Pierce Chemicals). Excess sites on the plastic were blocked using 1% (w/v) bovine serum albumin in PBS for 1 hr at room temperature. Plates were then washed ten times with 0.05% (w/v) TWEEN 80 in 0.15 mol/l sodium chloride. TWEEN is the trade name of a series of general-purpose emulsifiers and surface active agents that are polyoxyethylene derivatives of fatty acid partial esters of sorbitol and hydrides. Similar results have been obtained with maleic anhydride activated plates (Pierce Chemicals).

Mouse sera to be tested were diluted 1 in 1000 in diluent consisting of 0.5% (w/v) TWEEN 80.0.15 mol/l sodium chloride, 0.05 mol/l phosphate buffer pH 7 and 1% (w/v) bovine serum albumin diluent. Hybridoma supernatants for screening were diluted 1 in 2 in this diluent. Primary antibody binding was allowed to take place for 18 hr at room temperature. Then the plate was washed and peroxidase labelled anti-mouse IgG/peroxidase conjugate (1 in 1000) was added for 30 mins. After a final wash 0.1 ml of peroxidase TMB substrate (Dynatek) was added. Absorbances were read on a Dynatek mini reader of 405 nm after a 1 hr incubation period.

Cell Fusion

One of the two high responding mice immunized with peptide 9 was boosted intravenously and the spleen used to carry out a fusion. The mouse was injected IV with peptide 9/Tuberculin on each of the 4 days before fusion. The fusion was plated out over 20 microplates (1920) wells). After about 10 days, there were 1–3 clones growing in each well. After screening by ELISA on plates coated with 32 KDa inhibin only eight positives were observed. Eventually six stable clones were obtained. Five of these were isotyped as 1 gM and the remaining clone designated E4 made an IgG2b. Clone E4 could be grown as ascites with 1.5–2 mg/ml of specific antibody. The antibody could be purified on protein A without loss of activity provided it was promptly neutralised after elution at pH 3.5. Growth in a hollow fibre bioreator produced 2 mg/ml of antibody and the clone was stable.

Immunoconcentrations

Inhibin forms were concentrated from 200 ml of bovine follicular fluid using the monoclonal antibody to the α subunit (see later). The antibody was attached to Affigel. The inhibin forms were eluted to 6 M guinidine-HCl, dialysed against 0.063 mol/l Tris-Cl pH 6.75, and then treated with 1% (w/v) sodium dodecyl sulphate and 1 (w/v) mercaptoethanol before heating at 100 degrees for 5 minutes. The follicular fluid forms from 200 ml of follicular fluid were eventually in 4 ml of solution.

Electrophoresis and blotting

One microliter samples of the reduced and denatured preparation were electrophoresed on a pre-prepared 20% (w/v) homogenous sodium dodecyl sulphate polyacrylamide gels obtained from Pharmacia. Electrophoresis was carried out on a Pharmacia Phastsystem. In each run biotinylated molecular weight markers from Sigma were used alongside the inhibin preparations. After electrophoresis Phastsystem was used to transfer a blot of the gels onto nitrocellulose by diffusion blotting at elevated temperature as described in the Phastsystem manual. Subsequently, the blot was developed by successive incubations either with clone E4 (made here and reactive with the β subunit), or clone R1 (made previously and reactive with the α subunit; After this, followed biotinylated anti-mouse IgG (Serotec) and a histochemical stain for the location of alkaline phosphatase activity. Molecular weight calculations were made from enlarged photographs of the blots. The monoclonal antibody from clone E4 gave two bands corresponding to two different molecular weight forms of the β-A subunit.

Inhibition ELISA

A concentration of clone E4 antibody sufficient to produce in the ELISA as an absorbance of 0.6 was preincubated overnight at 4° C. with various dilutions of bovine follicular fluid prior to ELISA to determine whether the monoclonal antibody would react with the forms of inhibin (or activin) present in this fluid.

Preparation of Antibody to α sub-unit (R1)

Human and Animal Fluid Samples

Pooled BFF was obtained from ovaries supplied by Midland Meat Packers, Crick, Northamptonshire. Ovaries were transported back to the laboratory on ice and fluid aspirated within 4 hours of slaughter. Pooled HFF from women undergoing hyperovolution treatment was obtained from Bourne Hall Clinic, Hourne, Cambridgeshire. Both fluids were stored in aliquots at −40° C. Human post-menopausal serum from a 63 year old woman was obtained via the Blood Transfusion Laboratories, Oxford.

Synthetic Peptides and 32K Bovin Inhibin

As described in Groome et al HYBRIDOMA 9 31–42 (1990) synthetic peptides used were based on published sequences near the amino terminal of the 32K inhibin α subunit human 1–32 (for immunizations) was synthesized using pentafluorophenyl esters as described in a series of articles by Atherton and Sheppard and coworkers eg Eberley et al. (J. Chem. Soc. Perkin Trans. (1986) 361–367). Reagents for peptide synthesis were obtained from Milligen U.K. Millipore House, 11–15 Peterborough Road, Harrow. The Pennisula peptides were not purified further. All the peptides made here were purified by HPLC and the amino acid composition checked before use.

Purified bovin 12K inhibin was purchased from Pennisula Laboratories.

Coupling of Peptides to Carrier Proteins

Human 1–32 was coupled to tuberculin (PPD) via the cysteine using a heterofunctional agent. These couplings were carried out initially with reagents and protocols obtained from Cambridge Research Biochemicals Ltd, Button End, Harston, Cambridge. Tuberculin can be obtained from the Central Veterinary Laboratory, Weybridge.

Immunization of Mice

Adult intact male Balb/c mice (Harlan-Olac Ltd. Station Road, Blackthorn, Bicester) were primed by one dose of human BCG vaccine (Glaxo) subcutaneously. One month later 50 µg of human peptide 1–32 as a tuberculin conjugate was injected subcutaneously in Freund's incomplete adjuvant. Boosting with the same amount of immunogen in Freund's incomplete adjuvant was given on four occasions at monthly intervals. The highest responding mice were assessed by ELISA and set aside for fusions. The fusion described here used a mouse that had received its last boost 3 months previously.

Preparation of Monoclonal Antibodies

On each of the four days before fusion, 100 µg of immunogen was given in saline by intravenous injection into the tail vein. The spleen was removed and used for fusion of lymphocytes to SP2/0 myelomas by standard protocols. The fusion was screened by ELISA on plates coated with porcine 1–32 peptide as described in a later section. Isotyping was done using a commercial isotyping kit based on red cell agglutination (Serotec Ltd). The antibody was purified from ascites by protein A chromatography. The clone R1 produced a mouse IgG2a and could also be grown in a hollow fibre bioreactor producing 2 mg/ml of antibodies.

Growth of hybridoma clones used for Inhibin Assay

Clone R1

Clone R1 producing antibody to the Inhibin α sub-unit. Spleen cell patent was a Balb/c mouse. Myeloma line was SP2/0. Cells are routinely grown in Iscove's Modified Dulbecco's medium (IMDM) obtained from Gibco containing 20% v/v foetal calf serum (Gibco) and 50 micrograms/ml gentamycin. Gas phase is 5% CO2 in air.

This clone grows well as mouse ascites producing about 2 mg of antibody/ml of ascites or in a hollow fibre bioreactor producing up to 2 mg/ml. The antibody is IgG2a.

Clone E4

Clone E4 is the beta-A sub-unit. Spleen cell parent was Balb/c mouse. Myeloma line was SP2/0. Cells are routinely grown in Iscove's modified Dulbecco's medium containing 20% foetal calf serum (Gibco) and 50 micrograms/ml gentamycin. Gas phase is 5% CO2 in air.

This clone is a low producer in mouse ascites (0.5 mg-1 mg/ml) but grows well in hollow fibre bioreactors producing up to 2 mg/ml. The antibody is IgG2b.

Reagents and Procedures in accordance with the invention
TWO SITE ENZYME IMMUNOASSAY OF DIMERIC HUMAN INHIBIN IN FEMALE SERUM OR PLASMA
ASSAY PERFORMANCE The antibodies needed for these assays are provided in a form which enables the user to coat and use 20 microplates for the assay of dimeric inhibin in human serum and plasma. This will enable the researcher to assay at least 800 serum/plasma samples. Further complete commercial assay kits are now available to the investigator (Serotec Ltd), supplying all the necessary preprepared reagents with detailed instructions.

The assay can detect as little as 2 pg/ml of recombinant inhibin spiked into human serum. Most post-menopausal women have less than 5 pg/ml, whereas following ovarian hyperstimulation levels can reach 1200 pg/ml. Throughout the normal cycle levels are in the approximate range 3–120 pg/ml. Under optimal conditions the inter and intraplate coefficients of variation for sample duplicates are both less than 7%. Serial dilution of samples containing high levels of immunoreactivity behave identically to recombinant 32 k inhibin diluted in postmenopausal serum. Quantitative recovery of spiked inhibin is observed both in the follicular and luteal phase of normal cycles.

PROTOCOL FOR THE ENZYME IMMUNOASSAY OF DIMERIC INHIBIN IN HUMAN SERUM AND PLASMA
MATERIALS PROVIDED

1. Purified IgG from monoclonal antibody (E4) reacting with the beta-A subunit of inhibin. 1 ml of a 1 mg/ml solution.

2. Fab-alkaline phosphatase conjugate of a monoclonal antibody (R1) reacting with the α subunit of inhibin. The optimum concentration of this conjugate varied between batches and was determined by trial and error.

3. Recommended procedures, and step-by-step protocol.

NOT PROVIDED

1. Avidplate-HZ flat bottom. Obtained from Bioprobe International, 14272, Franklin Avenue, Tustin, Calif. 92680, USA.

In the UK these plates can be obtained from Quantum Biosystems, 12 Pembroke Avenue, Cambridge, CB5 9PB.

2. AMPAK kit for amplification of the alkaline phosphatase assay. 1 kit provides assay reagents for 4 microplates. Obtained from Dako Corporation, 6392 Via Real, Carpinteria, Calif. 93013. In the UK these kits can be obtained from Dako UK Ltd, 16 Manor Court Yard, Hughenden Avenue, High Wycombe, Bucks UK.

3. Recombinant inhibin standard. The WHO is presently preparing a standard of recombinant human 32K inhibin and many inhibin workers will have obtained such material for their previous work. A pool of serum from women undergoing ovulation induction could be used to prepare standards for in-house use, and this would simply need to be calibrated against a recombinant standard.

4. Hydrogen peroxide 30% (w/v). Use fresh analytical grade reagent.

5. A pool made of serum or plasma from post-menopausal women pretested in the assay and shown to contain undetectable dimeric inhibin. Approximately half of all post-menopausal sera would be suitable. Samples pooled should be free of hemolysis. Fetal calf serum has also been shown to be free from dimeric inhibin and may be used in substituted for post-menopausal serum as a diluent.

COUPLING OF E4 ANTIBODY TO AVIDPLATES

This procedure is designed to minimise losses of the E4 antibody during the coupling procedure.

1. You are provided with 1 ml of E4 antibody at a concentration of 1 mg/ml.

2. Transfer the solution to the minimum length of benzoylated dialysis tubing (Sigma catalog no D2272 holds 10 ml/foot). Do not boil the dialysis tubing before use. Just wash it with water. We find losses of antibody are lower with this tubing than conventional dialysis tubing.

3. Dialyze the antibody against three changes of 50 mM acetate buffer pH 5.0 in the cold room.

4. Make up a 100 mM solution of sodium periodate (21 mg/ml).

5. Find out what volume of antibody solution you have after dialysis by weighing the liquid removed from the sac.

6. Add 0.1 volume of the periodate reagent to give a final concentration of 10 mM.

7. Incubate the solution in the dark for 30 min at room temperature to allow aldehyde groups to be generated on the carbohydrate residues on the Fc of the antibody.

8. Stop the reaction by adding 0.01 volume of ethylene glycol.

9. Desalt the solution back to 50 mM acetate buffer pH 5.0 on a short (15 ml bed volume) Sephadex G25 column. Detect the antibody as the first peak by reading fractions at 280 nm. Alternatively dialyze overnight against two changes of acetate buffer (1 liter) in the cold room for 24 hours.

10. Read the final absorbance in a 1 cm cell. Antibody concentration in mg/ml will be absorbance/1.4.

11. Decide how much antibody in total you have and state this in micrograms. At the end of this procedure you will probably have around 600 micrograms of antibody. To coat the hydrazide plates we use a concentration of 5 micrograms/ml. Thus you have enough to make 600/5=120 ml of coating solution.

12. Add all the antibody to 120 ml of 50 mM acetate buffer pH 5.0 and mix thoroughly.

13. Avidplates-HZ wells are coated with 50 microliters overnight at room temperature. Place the plates in a box containing moist paper towelling to prevent evaporation during this procedure. You will have at least sufficient reagent to coat 20–24 microplates. Complete recovery of inhibin from serum matrix require a high density of functional E4 antibody and we do not recommend using a lower concentration than that stated here.

14. Make up a solution containing 0.1 M Tris-HCl pH 7.5 buffer, 1% BSA (Sigma protease free A3294), and 0.1% sodium azide.

15. One plate at a time, bang the plate dry on paper towelling and add 150 microliters of the above solution.

16. Plates can now be stored in the cold room for periods of at least 3–6 months and still give good results. Evaporation must be prevented.

17. Immediately before use the plate is washed on a plate washer with a wash solution consisting of 0.05% (w/v) Tween 20, 0.15 M NaCl, in 0.05 M Tris pH 7.5. (wash solution)

THE ASSAY PROCEDURE FOR HUMAN SERUM MATRIX FOR STANDARDS

1. To dilute your standards and unknowns you will need some serum from a post-menopausal woman (PMS) or fetal calf serum, both of which are free from dimeric inhibin-A.

Note approximately half of all PMS sera have no detectable inhibin in the assay described. Others give a low but significant signal (<5 pg/ml). We are presently working to determine if this small signal is non-specific or due to real inhibin. This is done by seeing if the signal can be blocked by preincubating the Fab R1, alkaline phosphatase conjugate with the synthetic peptide immunogen used to make R1 before adding it to the well. If the signal can be blocked it is probably due to inhibin. If not it may be due to heterophile antibodies in that sample. Further information on this subject will be provided as it becomes available.

FIND YOURSELF AN APPRECIABLE VOLUME OF SERUM GIVING AS LOW A SIGNAL, AS POSSIBLE. This must be free of hemolysis.

INHIBIN FOR STANDARDS

Recombinant inhibin standards are made in the selected post-menopausal serum pool and stored at −80° C.

ASSAY DILUENT

5% (w/v) Triton X100 (Sigma X100)

10% (w/v) Bovine serum albumin (protease free, Sigma A3294)

5% (v/v) Normal mouse serum (Serotec Product code C1158)

All in 0.1 M Tris-HCL pH 7.5, 0.15 M sodium chloride.

Let it all stir on a stirrer for a few hours until it is clear.

Filter this solution through a 0.2 micron filter. It helps the filter if you remove the lumps by centrifugation or a prefilter (millex from millipore).

Then add sodium azide to 0.1% (its safer than filtering azide) and store the solution in the cold room. For longer term storage keep the unfiltered solution in the freezer, and filter and add azide in 100 ml lots as needed.

ASSAY PROCEDURE

1. Make up standard recombinant inhibin concentrations in selected post-menopausal serum (PMS) from 500 pg/ml down to around 2 pg/ml.

2. Put 0.1 ml amounts of each standard or unknown sample in a small tube and two 0.1 ml aliquots of just PMS in another two tubes.

It is important that serum or plasma samples from pregnant women are free of hemolysis are obtained by gentle collection procedures. Excessive hemolysis will impair the action of the hydrogen peroxide, and give underestimates of the amount of inhibin dimer. Similarly, the post-menopausal serum used as a matrix for standards and a diluent for unknowns must also be free of hemolysis. Serum/plasma samples taken during pregnancy will require dilution by approximately 10 told to bring them into the accurate region of the standard curve. They are diluted in the post-menopausal serum before the hydrogen peroxide treatment and then processes as described for the standards.

3. Make up freshly a 5% (w/v) aqueous solution of hydrogen peroxide and add 25 microliters to each tube. Mix gently. Oxygen bubbles will appear in the tube, sometimes more than others. This treatment is designed to oxidase the methionine residues in the epitope for the E4 antibody. This follows an observation that the affinity of interaction of inhibin with this antibody is increased by this method. It improves assay sensitivity by about 0 fold—8 fold depending on the state of oxidation of inhibin in the sample to start with. Note that samples and standards in the assay are both treated identically.

4. After a 30 min reaction period add 0.2 mls of assay diluent to each tube. Mix.

5. Take an E4 coated hydrazide plate, (prepared as above) and wash it ten times with 0.05% (w/v) TWEEN 20, 0.15 M NaCl, in 0.05 M Tris-HCl pH 7.5. Bang the plate dry on tissue.

6. Without delay add 0.08 ml of each sample or standard to duplicate wells on the microplate.

Each plate must have a standard curve and precautions taken to make sure that evaporation or temperature gradients do not occur during the assay. Look out for any signs that the edge wells give abnormal readings.

7. Incubate the plate overnight in the cold room. We have it shaking but this may not be essential.

8. Wash the plate 4 times with wash solution. Immediately add 50 microliters of 1 in 400 dilution of the Fab R1 alkaline phosphatase conjugate.

9. Shake at room temperature for 1–2 hr. Make sure the plate is covered.

AMPLIFIED ELISA

Detection uses an amplification of the alkaline phosphatase reaction. However, equivalent results can be obtained without amplification using a simple alkaline phosphatase substrate such as p-nitrophenyl phosphate.

PROCEDURE WITH AMPAK KIT

N.B. Thorough washing procedures are critical to the method.

1. After the incubation with the alk phos conjugated antibody above, wash the plate ten times on the plate washer. Hang dry.

2. Make up a 1 in 12 dilution in water of the AMPAK wash solution which comes with the kit. This is specially formulated to reduce non-specific binding. We wash the plate twice more manually with this solution allowing it to shake for two 15 minute periods in each.

Make sure the stock of this does not get in touch with alk phos conjugate.

3. Bang the plate and add kit substrate. (50 µl/well)

We make up all the kit substrate at one time. In order to allow the substrate reaction to run for longer we add additional magnesium to the substrate (1 µl/ml of 1 M MgCl1). Following advice from the manufacturers (Dako). We aliquot the substrate solution in 6 ml amounts each sufficient for 1 microplate, and store these frozen.

4. Cover the plate with parafilm and shake it at 37° C. for 2 h. To secure the parafilm we put a lid on the plate. It is important that at this stage the plate is not subjected to temperature gradients, or the outer wells to evaporation.

5. Remove the plate from the incubator and allow it to return to room temperature for ten minutes.

6. Add 50 microliters of kit amplifier. This is also made up in advance and stored frozen in 6 ml amounts. Because colour development is so fast this must be added to the wells in a timed sequence (eg 1 row each 5 sec). When all the wells have had amplifier added tap the plate gently to mix and allow it to stand for 3–10 minutes until the post-menopausal wells start to develop visible colour.

7. Stop the reaction by adding 50 microliters of kit stop solution in the same timed sequence as amplifier.

8. Read the plate at 490 nm with a reference wavelength of 620 nm. Most ELISA readers will plot your standard curve.

9. Serum samples from hyperovulated or pregnant women can have more than 1000 pg/ml and will need to be diluted with PMS into the accurate region of the standard curve.

10. The plates are easy to photograph and can be stored frozen if they cannot be read or photographed directly.

ASSESSMENT OF ASSAY PERFORMANCE

1. Excellent recovery of recombinant 32 k inhibin spiked into human serum and plasma or even blood.

2. Works for both serum and heparinised plasma with insignificant difference in levels.

3. Samples from hyperovulated women dilute out closely parallel to the 32 k standards in PMS as do samples from women at the peak of the luteal phase in a normal cycle.

4. The assay has been validated for human female samples.

5. Activin and tree α subunits have less than 0.1% cross-reactivity in the assay following the procedures described.

6. A typical specimen set of results for the assay of recombinant standards diluted in postmenopausal serum is shown below in Table 1.

| Concentration of recombinent standard in serum from post-menopausal woman | | |
|---|---|---|
| Picograms/ml | Absorbances | Estimated concentration from fitted standard curve |
| 0 | 0.057, 0.53, 0.051, 0.057 | |
| 2 | 0.091, 0.089 | |
| 3.9 | 0.117, 0.122 | 4.3 |
| 7.8 | 0.170, 0.169 | 8.3 |
| 15.6 | 0.281, 0.294 | 16.4 |
| 31.21 | 0.496, 0.510 | 30.2 |

-continued

| Concentration of recombinent standard in serum from post-menopausal woman | | |
|---|---|---|
| Picograms/ml | Absorbances | Estimated concentration from fitted standard curve |
| 62.5 | 0.925, 0.935 | 62.5 |
| 125 | 1.387, 1.434 | 125 |

The invention will no be further described by comparing the prior methods of assay in both the first and second trimester with that of the present invention.

First Trimester

Previously, we have studied two different immunoreactive inhibin assays respect to the detection of Down's syndrome in the first trimester. One used an antibody raised against 31 kD bovine inhibin and the other, a commercial two-site assay, using two antibodies directed against 2 distinct α-subunit epitopes. The first assay was a heterologous radioimmunoassay using an antibody (1989) raised against 31 kDa bovin inhibin and a tracer of iodinated 31 kDa bovine inhibin. Recombinant human inhibin-A (rhINH-R-90/1) was used for standards with the results expressed as pg/ml. The sensitivity of the assay was 780 pg/ml and the coefficients of variation of intra-assay and inter-assay were 6.6% and 11.5% respectively. This assay is now distributed by the National Institute of Child Health and Human Development (NICHD).

The second assay, a commercial solid-phase two site immunoenzymatic assay (Medgenix, High Wycombe UK) was used to assay the same samples. The two antibodies employed in this assay were directed against distinct epitopes of the a-subunit of human inhibin. Human inhibin was used as standards and the results were expressed as U/ml. The sensitivity of the assay was 0.1 U/ml and the coefficients of variation of intra-assay and inter-assay were 1.9% and 8.9% respectively.

These were evaluated using maternal serum from 11 women with an identified Down's affected pregnancy and 44 controls (4 matched to each Down's sample by gestation and duration-of-storage). 5 of the Down's samples had been collected at 11 weeks and 6 at 12 weeks.

Using the NICHD Assay, the mean (±SEM) maternal serum immunoreactive inhibin at 11 and 12 weeks gestation in the Down's syndrome samples were 3186±195 pg/ml and 2517±441 pg/ml and in the controls 2020±172 pg/ml and 2561±198 pg/ml respectively. The mean immunoreactive inhibin levels at the two gestations were not significantly different for either group, and there were no significant differences between Down's syndrome and normal pregnancies (2821±267 pg/ml and 2317±138 pg/ml respectively, n.s.).

Using the Medgenix Assay, the mean (±SEM) maternal serum immunoreactive inhibin at 11 and 12 weeks gestation in the Down's syndrome samples were 2.46±0.56 U/ml and 2.35±0.62 U/ml and in the controls 1.84±0.17 U/ml and 2.20±0.33 U/ml respectively. The mean immunoreactive inhibin levels at the two gestations were not significantly different for either group, and there were no significant differences between Down's syndrome and normal pregnancies (2.4±0.4 U/ml and 2.04±0.19 U/ml respectively, n.s.).

Further, there was poor correlation between the inhibin levels derived from the two assays.

In conclusion statistical analysis of the data revealed that neither assay detected a significant effect of gestation on serum inhibin levels. After combining the data from both gestations, no significant difference between the Down's samples and controls for either assay was detected. These data suggest that these two assays detect different inhibin species in pregnancy serum but that neither will be useful for the detection of Down's syndrome in the late first trimester. In contrast, we have now established that inhibin-A is an extremely good marker for Down's syndrome in the first trimester.

23 women were identified from records of known Down's affected pregnancies allowing their stored serum to be retrieved. The sera from 8 of these women had been collected at 11 completed weeks of gestation, 8 at 12 completed weeks and 7 at 13 completed weeks. These gestations had been calculated from ultrasound scans performed on the day of sampling. Similarly, for each Down's affected sample 4 control women, matched for gestation (ultrasound determined) and duration of storage, were identified and their samples retrieved. Three control samples, one each matched for three different 11 week Down's samples, were unable to be used due to insufficient sample volume, making 89 control samples available for assay.

In these samples from the first trimester the mean (95% CI) maternal serum dimeric inhibin A in the control samples was 389.5 (341.3–437.7) pg/ml, 341.3 (279.9–402.7) pg/ml and 263.6 (218.7–308.4) pg/ml at 11, 12 and 13 weeks respectively. In the Down's syndrome samples the median MoM was 2.46 (95% CI 2.11–3.26) and for a given FPR of 5%, 65% (15/23) of the Down's Syndrome samples were detected (Table 1). FIG. 1 shows the 10th, 50th and 90th centiles for the 23 Down's syndrome cases plotted as MoMs.

The novel data presented indicate that maternal serum dimeric inhibin-A is a useful serum marker of Down's syndrome in the first trimester of pregnancy.

Second Trimester

In the second trimester, only the Medgenix assay has been evaluated. These data have been alluded to earlier. In the first report (van Lith et al 1992) it was shown that immunoreactive inhibin was elevated in association with Down's syndrome. Subsequently, one other report has confirmed this. However, it was suggested that the wide distribution of inhibin levels in both the control and Down's syndrome pregnancies made it unlikely that inhibin, as detected, would be a valuable marker.

Figure 2:
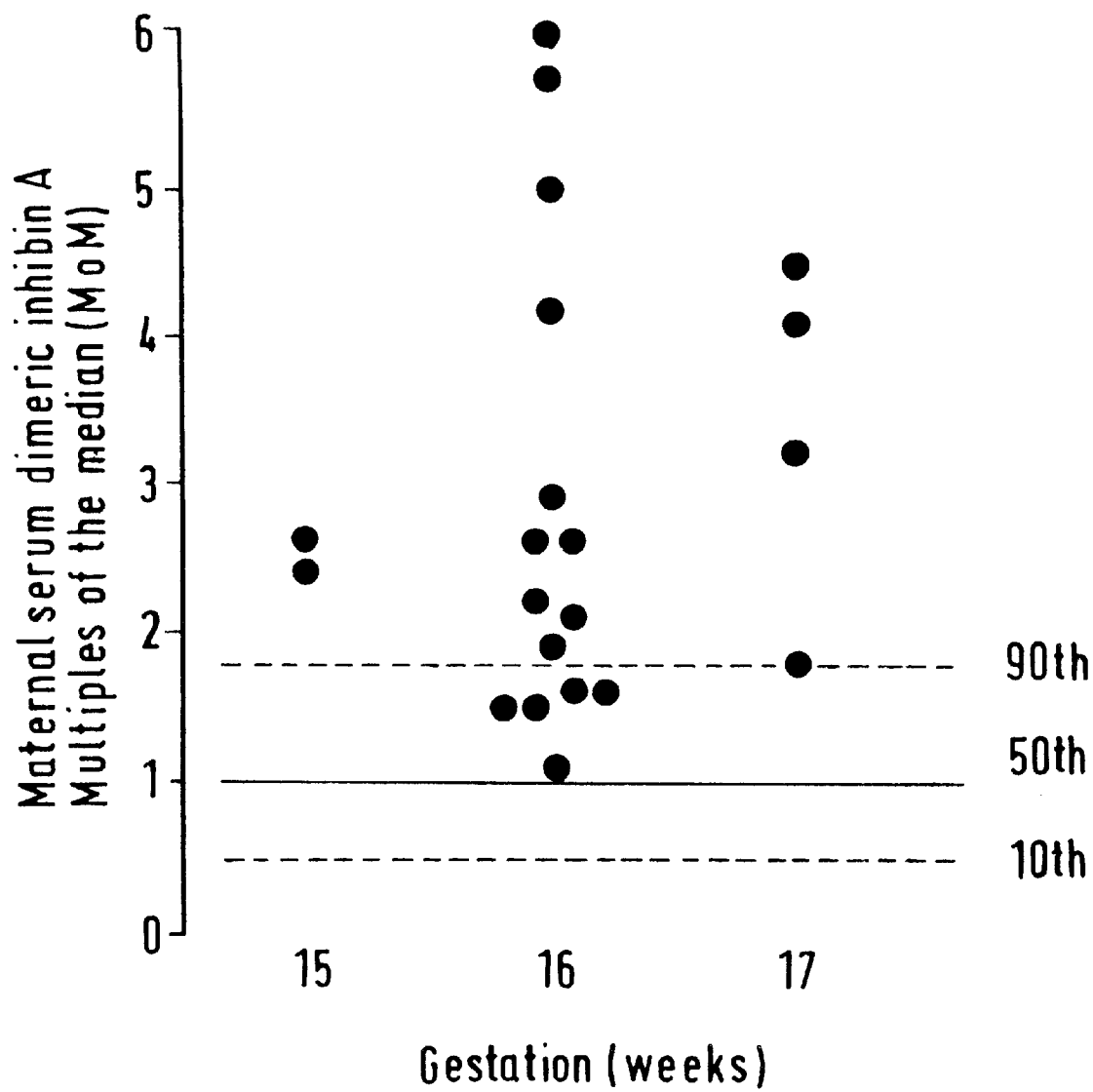

This invention details data showing for the first time that, as in the first trimester, in the second trimester inhibin-A is significantly elevated to a degree that would offer high detection rates of Down's syndrome. In 21 Down's syndrome pregnancies at 15–17 weeks, the inhibin-A median MoM was 2.6, calculated from 150 normal pregnancies (FIG. 2). It was calculated that for a given FPR of 5.3% a detection rate of 62% would be afforded (Table 2).

Thus, in both the first and second trimesters, elevated levels of dimeric inhibin-A have been shown to be an indication of Down's syndrome. The levels required to indicate positive results may be further refined as development of the test proceeds. The increase is a marked increase e.g. up to twice the levels of normal pregnancies. These results are very different from those reported on the other non-specific inhibin assays, both in the first and second trimesters.

TABLE 1

Number (percentage) of affected and unaffected pregnancies in the first trimester (11–13 weeks) with a given MoM above different arbitrary levels.

| MoM | Number (%) of Affected Pregnancies | Number (%) of Unaffected Pregnancies |
| --- | --- | --- |
| 0.5 | 23 (100) | 86 (97) |
| 1.0 | 22 (96) | 42 (47) |
| 1.5 | 19 (83) | 18 (20) |
| 2.0 | 15 (65) | 6 (7) |
| 2.5 | 10 (43) | 1 (1) |
| 3.0 | 9 (39) | 1 (1) |
| 3.5 | 5 (22) | 0 (0) |
| 4.0 | 4 (17) | 0 (0) |
| 4.5 | 3 (13) | 0 (0) |

TABLE 2

Number (percentage) of affected and unaffected pregnancies in the second trimester (15–17 weeks) with a given MoM above different arbitrary levels.

| MoM | Number (%) of Affected Pregnancies | Number (%) of Unaffected Pregnancies |
| --- | --- | --- |
| 0.5 | 21 (100) | 135 (90) |
| 1.0 | 21 (100) | 76 (51) |
| 1.5 | 21 (100) | 28 (19) |
| 2.0 | 14 (67) | 11 (7) |
| 2.5 | 11 (52) | 4 (3) |
| 3.0 | 7 (33) | 1 (1) |
| 3.5 | 6 (29) | 0 (0) |
| 4.0 | 6 (29) | 0 (0) |
| 4.5 | 4 (19) | 0 (0) |

Legends to Figures

FIG. 1. The 10th, 50th and 90th percentiles of maternal serum inhibin-A MoMs of 89 chromosomally normal pregnancies with levels from 23 individual Down's affected pregnancies.

FIG. 2. The 10th, 50th and 90th percentiles of maternal serum inhibin-A MoMs of 150 chromosomally normal pregnancies with levels from 21 individual Down's syndrome pregnancies.

We claim:

1. A method of testing for indications of Down's syndrome which comprises measuring the level of inhibin-A in a sample of maternal body fluid taken during gestation, which inhibin-A comprises an α-sub-unit and a β-sub-unit (βA).

2. A method according to claim 1, which is specific for Inhibin-A.

3. A method according to claim 1, in which said method comprises the use of an antibody (βA antibody) specific for the inhibin-A β sub-unit (βA sub-unit).

4. A method according to claim 3 in which the βA antibody is a monoclonal antibody, said monoclonal antibody is derived from a hybridoma, which is prepared using a peptide corresponding to a part of the βA sub-unit as an immunogen.

5. A method according to claim 4, in which the peptide is a synthetic peptide corresponding to part of a C-terminal region of the βA sub-unit.

6. A method according to claim 3, in which the βA antibody is used to capture inhibin-A from a test sample.

7. A method according to claim 1, in which the method comprises the use of an antibody specific for Inhibin-A α sub-unit.

8. A method according to claim 7, in which α sub-unit antibody is derived from a hybridoma, which is prepared using a peptide corresponding to a part of the inhibin-A α sub-unit as an immunogen.

9. A method according to claim 8, in which the peptide is a synthetic peptide corresponding to part of an N-terminal region of the α sub-unit.

10. A method according to claim 8, in which a Fab fragment of the antibody is used.

11. A method according to claim 7, in which the α sub-unit antibody is used as a detection antibody and is linked to a detectable marker.

12. A method according to claim 11, in which the detection antibody is enzyme-linked.

13. A method according to claim 1, in which the maternal body fluid is serum or plasma.

14. A method according to claim 1, carried out in the first trimester of gestation.

15. A method according to claim 14, carried out from the eleventh to the thirteenth week of gestation.

16. A method according to claim 1, carried out in the second trimester of gestation.

17. A method according to claim 1, carried out as a screening test to select patients for subsequent diagnostic testing.

18. A method according to claim 17, carried out as an adjunct to the assay of other markers.

19. A reagent kit for screening for Down's Syndrome comprising a first antibody specific for a β sub-unit of inhibin-A and a second antibody specific for an α sub-unit of inhibin A.

20. A reagent kit according to claim 19, in which the first antibody is attached to a support material.

21. A reagent kit according to claim 19, in which the second antibody is linked to a detectable marker.

* * * * *

UNITED STATES PATENT AND TRADEMARK OFFICE
CERTIFICATE OF CORRECTION

Page 1 of 2

PATENT NO : 5,952,182

DATED : September 14, 1999

INVENTOR(S) : Nigel Patrick Groome; Euan Morrison Wallace

It is certified that error appears in the above-identified patent and that said Letters Patent is hereby corrected as shown below:

In column 1, lines 39 and 40, please change "gonadotrophial" to --gonadotrophin--.

In column 1, line 44, please change "otter" to --offer--.

In column 2, line 63, please change "sub=unit" to --sub-unit--.

In column 6, line 29, please change "IgG" to --1gG--.

In column 6, line 29, after "(Serotec)", please insert --, streptavidin/alkaline phosphatase (Serotec)--.

In column 6, line 49, please change "Hourne" to --Bourne--.

In column 6, line 66, please change "12K" to --32K--.

In column 8, line 12, please change "IgG" to --1gG--.

In column 8, line 24, after "Avenue,", please insert --Waterbeach,--.

In column 9, line 66, please change "C1158)" to --C115B)--.

In column 10, line 27, please change "processes" to --processed--.

In column 11, line 12, please change "MgC11)" to --MgC12)--.

UNITED STATES PATENT AND TRADEMARK OFFICE
CERTIFICATE OF CORRECTION

PATENT NO. : 5,952,182
DATED : September 14, 1999
INVENTOR(S) : Nigel Patrick Groome; Euan Morrison Wallace It is certified that error appears in the above-identified patent and that said Letters Patent is hereby corrected as shown below:

In column 11, line 12, please change "MgC11)" to --MgC12)--.

In column 12, line 10, please change "no" to --now--.

Signed and Sealed this

Nineteenth Day of September, 2000

Q. TODD DICKINSON

*Attest:*

*Attesting Officer*          *Director of Patents and Trademarks*